United States Patent
Vanoppen et al.

(10) Patent No.: US 7,618,917 B2
(45) Date of Patent: Nov. 17, 2009

(54) RUTHENIUM CATALYSTS

(75) Inventors: Dominic Vanoppen, Kapellen (BE); Melanie Maas-Brunner, Mannheim (DE); Ulrich Kammel, Speyer (DE); Jan-Dirk Arndt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 645 days.

(21) Appl. No.: 10/480,284

(22) PCT Filed: Jun. 10, 2002

(86) PCT No.: PCT/EP02/06346

§ 371 (c)(1), (2), (4) Date: Dec. 11, 2003

(87) PCT Pub. No.: WO02/100537

PCT Pub. Date: Dec. 19, 2002

(65) Prior Publication Data

US 2004/0176619 A1    Sep. 9, 2004

(30) Foreign Application Priority Data

Jun. 11, 2001   (DE) ................................ 101 28 205

(51) Int. Cl.
   *B01J 23/46*   (2006.01)
(52) U.S. Cl. ........................................ 502/326
(58) Field of Classification Search ............... None
See application file for complete search history.

(56) References Cited

U.S. PATENT DOCUMENTS

| | | | |
|---|---|---|---|
| 3,055,840 A | 9/1962 | Kock, Jr. | |
| 3,963,788 A | 6/1976 | Kruse et al. | |
| 3,963,789 A | 6/1976 | Kruse et al. | |
| 4,380,680 A | 4/1983 | Arena | |
| 4,413,152 A | 11/1983 | Arena | |
| 4,471,144 A | 9/1984 | Arena | |
| 4,487,980 A | 12/1984 | Arena | |
| 4,503,274 A | 3/1985 | Arena | |
| 4,577,566 A * | 3/1986 | Merrell | 110/343 |
| 4,950,812 A | 8/1990 | Jacobs et al. | |
| 5,334,790 A | 8/1994 | Richard et al. | |
| 5,414,171 A | 5/1995 | Richard et al. | |
| 5,945,571 A | 8/1999 | Pinkos et al. | |
| 6,177,598 B1 * | 1/2001 | Brunner et al. | 568/863 |

FOREIGN PATENT DOCUMENTS

| | | |
|---|---|---|
| EP | 0 992 475 | 4/2000 |
| FR | 2 526 782 | 11/1983 |
| RU | 2 147 298 C1 | 4/2000 |

OTHER PUBLICATIONS

A.J. Hong et al.: "Effect of silica support on Ru-Cu cluster morphology as determined by catalytic activity" Journal of Physical Chemistry, American Chemical Society, vol. 91. No. 10, pp. 2665-2671 May 7, 1987.
P. Moggi et al.: "Ru/Si02 catalysts prepared by the sol-gel method from Ru3(CO)12" Applied Catalysis A: General, vol. 182, No. 2, pp. 257-265 Jun. 21, 1999.
W. Zou et al.: "Pretreatment chemistry in the preparation of silica-supported PT, RU, and PT-RU catalysts: an in situ UV diffuse reflectance study" Journal of Catalysis, vol. 133, pp. 202-219, 1992.
H. Schiweck et al.: "Sugar alcohols" Ullmann'S Encyclopedia of Industrial Chemistry, 5$^{th}$ ed. vol. A25, pp. 413-437, 1994.

* cited by examiner

*Primary Examiner*—Yvonne L. Eyler
*Assistant Examiner*—Yevegeny Valenrod
(74) *Attorney, Agent, or Firm*—Oblon, Spivak, McClelland, Maier & Neustadt, L.L.P.

(57) ABSTRACT

Novel ruthenium catalysts can be obtained by:
   i) treating a support material based on amorphous silicon dioxide one or more times with a halogen-free aqueous solution of a low molecular weight ruthenium compound and subsequently drying the treated support material at below 200° C.,
   ii) reducing the solid obtained in i) by means of hydrogen at from 100 to 350° C.,
where step ii) is carried out directly after step i). These catalysts can be used for the catalytic hydrogenation of monosaccharides and disaccharides to produce sugar alcohols, with the exception of sorbitol.

13 Claims, No Drawings

RUTHENIUM CATALYSTS

BACKGROUND OF THE INVENTION

1. Field of the Invention

The present invention relates to novel ruthenium catalysts, to a process for producing them and to their use for the catalytic hydrogenation of monosaccharides and disaccharides in the preparation of sugar alcohols, with the exception of sorbitol.

2. Description of the Background

The industrial-scale preparation of sugar alcohols is generally carried out by catalytic hydrogenation of corresponding monosaccharides and disaccharides (cf. H. Schiweck et al. "Sugar Alcohols" in Ullmann's Encyclopedia of Industrial Chemistry, 5th ed. on CD-ROM). Catalysts used for this purpose have hitherto been, first and foremost, nickel catalysts, e.g. supported nickel catalysts or Raney nickel. As an alternative, the use of ruthenium-containing catalysts for this purpose has also been reported. In general, the ruthenium catalysts are supported catalysts in which the ruthenium is present on an oxidic or organic support such as carbon.

Thus, U.S. Pat. Nos. 4,380,680, 4,487,980, 4,413,152 and 4,471,144 describe catalysts which are suitable for the hydrogenation of carbohydrates to form the corresponding sugar alcohols and comprise ruthenium on a support material which is stable under hydrothermal conditions. Hydrothermal support materials proposed are alpha-aluminum oxide (U.S. Pat. No. 4,380,680), titanium(IV) oxide (U.S. Pat. No. 4,487,980), aluminum oxide treated with titanium(IV) halide (U.S. Pat. No. 4,413,152) and theta-aluminum oxide (U.S. Pat. No. 4,471,144).

U.S. Pat. No. 4,503,274 discloses catalysts which are suitable for the hydrogenation of carbohydrates to form the corresponding sugar alcohols and are produced by impregnating a support which is stable under hydrothermal conditions with an aqueous ruthenium halide solution and subsequently hydrogenating the solid at from 100 to 300° C.

U.S. Pat. No. 3,963,788 describes ruthenium catalysts which can be used for the hydrogenation of carbohydrates and in which the ruthenium is supported on a specific zeolite based on an aluminosilicate.

U.S. Pat. No. 3,963,789 proposes crystalline aluminosilicate clays, in particular montmorillonite, as supports for ruthenium catalysts.

FR-A 2526782 describes the use of a ruthenium chloride prepared by reaction of sodium chloride and ruthenium via $Na_2RuCl_6$ for producing ruthenium catalysts supported on silicon dioxide for the hydrogenation of monosaccharides and oligosaccharides.

The ruthenium catalysts known from the prior art have only moderate reactivities in the hydrogenation of carbohydrates, which results in low space-time yields of sugar alcohols, based on the catalyst used. In view of the high cost of ruthenium, the economics of these processes therefore leaves something to be desired. In addition, the selectivities of the catalysts are not satisfactory, so that an additional outlay is required for isolating the desired products. In particular, epimerization of the hydroxy groups is frequently observed.

SUMMARY OF THE INVENTION

It is an object of the present invention to provide novel, highly reactive catalysts for the preparation of sugar alcohols by catalytic hydrogenation of the corresponding carbohydrates. Furthermore, the catalysts should have a high product selectivity, particularly with a view to a continuous embodiment of the hydrogenation.

We have found that this object is achieved by ruthenium catalysts which are obtainable by:
i) treating a support material based on amorphous silicon dioxide one or more times with a halogen-free aqueous solution of a low molecular weight ruthenium compound and subsequently drying the treated support material at below 200° C., preferably ≦180° C. and in particular ≦150° C.,
ii) reducing the solid obtained in i) by means of hydrogen at from 100 to 350° C., preferably from 150 to 350° C. and in particular from 200 to 320° C., where step ii) is carried out directly after step i).

DETAILED DESCRIPTION OF THE PREFERRED EMBODIMENTS

The invention thus provides these catalysts and the process described here for producing them. The catalysts of the invention have improved activity and high product selectivity in the hydrogenation of monosaccharides and oligosaccharides.

It is presumed that the high activity of the catalysts of the present invention can be attributed to the particularly good distribution of the ruthenium over the surface of the support material and to the virtual absence of halogen in the support material. As a result of the method of producing the catalysts of the present invention, the ruthenium is present in them as metallic ruthenium. Examination of the catalysts of the present invention by transmission electron microscopy has shown that the ruthenium on the support material is present in atomically disperse form and/or in the form of ruthenium particles which are virtually exclusive, i.e. in a proportion of more than 90%, preferably more than 95%, based on the number of visible particles, present as isolated particles having diameters below 10 nm, in particular below 7 nm. In other words, the catalyst contains essentially no ruthenium particles and/or agglomerates of ruthenium particles having diameters above 10 nm, i.e. it contains a proportion of less than 10%, in particular less than 5%, of such particles and/or agglomerates. In addition, as a result of the use of halogen-free ruthenium precursors and solvents in the production of the catalysts of the present invention, the chlorine content of these catalysts is below 0.05% by weight (<500 ppm), based on the total weight of the catalyst. Here and in the text below, all ppm data are to be understood as meaning parts by weight, unless stated otherwise.

An important aspect of the catalysts of the invention is the use of a support material based on amorphous silicon dioxide. In this context, the term "amorphous" implies that the proportion of crystalline silicon dioxide phases in the support material is less than 10%. The support materials used for producing the catalysts of the invention can, however, have long-range structures formed by a regular arrangement of pores in the support material.

Suitable support materials are in principle all types of amorphous silicon dioxide which comprise at least 90% by weight of silicon dioxide, with the remaining 10% by weight, preferably not more than 5% by weight, of the support material being able to be made up of another oxidic material, e.g. MgO, CaO, $TiO_2$, $ZrO_2$, $Fe_2O_3$ or alkali metal oxide. It goes without saying that the support material used is likewise halogen-free, i.e. the halogen content is less than 500 ppm, based on the total weight of the support material. The support material preferably contains no more than 1% by weight, in particular no more than 0.5% by weight and particularly preferably no detectable amounts (<500 ppm), of aluminum oxide, calculated as $Al_2O_3$. In a preferred embodiment, support materials containing less than 500 ppm of $Fe_2O_3$ are used. The alkali metal oxide content generally results from the preparation of the support material and can be up to 2% by weight. It is frequently less than 1% by weight. Supports which are free of alkali metal oxide (<0.1% by weight) are also suitable. The proportion of MgO, CaO, $TiO_2$ and $ZrO_2$ can be up to 10% by weight of the support material and is preferably no more than 5% by weight. However, support materials which contain no detectable amounts of these metal oxides (<0.1% by weight) are also suitable.

Preference is given to support materials which have a specific surface area in the range from 50 to 700 $m^2/g$, in particular in the range from 80 to 600 $m^2/g$ and especially in the range from 100 to 600 $m^2/g$ (BET surface area in accordance with DIN 66131). Among pulverulent support materials, particular preference is given to ones whose specific (BET) surface area is in the range from 200 to 600 $m^2/g$. In the case of support materials in the form of shaped bodies, the specific surface area is, in particular, in the range from 100 to 300 $m^2/g$.

Suitable amorphous support materials based on silicon dioxide are well known to those skilled in the art and are commercially available (cf. for example, O.W. Flörke "Silica" in Ullmann's Encyclopedia of Industrial Chemistry 5th ed. on CD-ROM). They can be either of natural origin or can have been produced synthetically. Examples of suitable amorphous support materials based on silicon dioxide are kieselguhr, silica gels, pyrogenic silica and precipitated silica. In a preferred embodiment of the invention, the catalysts have silica gels as support materials.

Depending on the way in which the hydrogenation process in which the catalysts of the present invention are used is carried out, the support material can have differing shapes. If the process is carried out as a suspension process, the support material is usually used in the form of a finely divided powder for producing the catalysts of the present invention. The powder preferably has particle sizes in the range from 1 to 200 μm, in particular from 1 to 100 μm. When the catalyst is used in a fixed bed, it is usual to use shaped bodies of the support material which are obtainable by, for example, extrusion, ram extrusion or tableting and are, for example, in the form of spheres, pellets, cylinders, extrudates, rings or hollow cylinders, stars and the like. The dimensions of the shaped bodies are usually in the range from 1 mm to 25 mm. Use is frequently made of catalyst extrudates having extrudate diameters of from 2 to 5 mm and extrudate lengths of from 2 to 25 mm.

The ruthenium content of the catalysts of the invention can vary over a wide range. It is generally at least 0.1% by weight, preferably at least 0.2% by weight, and frequently does not exceed a value of 10% by weight, in each case based on the weight of the support material and calculated as elemental ruthenium. The ruthenium content is preferably in the range from 0.2 to 7% by weight, in particular in the range from 0.4 to 5% by weight.

The ruthenium catalysts of the present invention are generally produced by firstly treating the support material with a halogen-free aqueous solution of a low molecular weight ruthenium compound, hereinafter referred to as (ruthenium) precursor, in such a way that the desired amount of ruthenium is taken up by the support material. This step will hereinafter also be referred to as impregnation. The support which has been treated in this way is subsequently dried while maintaining the abovementioned upper temperature limits. The solid obtained in this way may, if necessary, then be treated again with the aqueous solution of the ruthenium precursor and dried again. This procedure is repeated until the amount of ruthenium compound taken up by the support material corresponds to the desired ruthenium content of the catalyst.

The treatment or impregnation of the support material can be carried out in various ways and depends, as is known, on the physical form of the support material. For example, the support material can be sprayed with the precursor solution, the precursor solution can be passed over it or the support material can be suspended in the precursor solution. For example, the support material can be suspended in the aqueous solution of the ruthenium precursor and filtered from the aqueous liquid after a certain time. The ruthenium content of the catalyst can then be controlled in a simple manner via the amount of liquid taken up and the ruthenium concentration of the solution. Impregnation of the support material can also be carried out by, for example, treating the support with a defined amount of the aqueous solution of the ruthenium precursor which corresponds to the maximum amount of liquid which can be taken up by the support material. For this purpose, the support material can, for example, be sprayed with the desired amount of the liquid. Suitable apparatuses for this purpose are the apparatuses customarily used for mixing liquids with solids (cf. Vauck/Müller, Grundoperationen chemischer Verfahrenstechnik, 10th Edition, Deutscher Verlag für Grundstoffindustrie, 1994, p. 405 ff.), for example tumble dryers, impregnation drums, drum mixers, blade mixers and the like. In the case of monolithic supports, the aqueous solutions of the ruthenium precursor are usually passed over the support.

The aqueous solutions used for impregnation are, according to the present invention, halogen-free, i.e. they contain no halogen or less than 500 ppm, preferably less than 100 ppm, of halogen, based on the total weight of the solution. For this reason, the ruthenium precursors used are ruthenium compounds which contain no chemically bound halogen and are sufficiently soluble in the aqueous solvent. These include, for example, ruthenium(III) nitrosyl nitrate ($Ru(NO)(NO_3)_3$), ruthenium(III) acetate and alkali metal ruthenates(IV) such as sodium or potassium ruthenate(IV).

In the present context, the term "aqueous" refers to water and mixtures of water with up to 50% by volume, preferably no more than 30% by volume and in particular no more than 10% by volume, of one or more water-miscible organic solvents, e.g. mixtures of water with $C_1$-$C_4$-alkanols such as methanol, ethanol, n-propanol or isopropanol. Water is frequently used as sole solvent. The aqueous solvent will frequently further comprise at least one halogen-free acid, e.g. nitric acid, sulfuric acid, phosphoric acid or acetic acid, preferably a halogen-free mineral acid, for stabilizing the ruthenium precursor in the solution. In many cases, a halogen-free mineral acid diluted with water, e.g. dilute to half-concentrated nitric acid, is therefore used as solvent for the ruthenium precursor. The concentration of the ruthenium precursor in the aqueous solutions naturally depends on the amount of ruthenium precursor to be applied and to the uptake capacity of the support material for the aqueous solution and is generally in the range from 0.1 to 20% by weight.

Drying can be carried out at the abovementioned upper temperature limits using customary methods of solids drying. Adherence to the upper limit prescribed according to the present invention for the drying temperatures is important for the quality, i.e. the activity, of the catalyst. Exceeding the abovementioned drying temperatures leads to a significant loss of activity. Calcination of the support at higher temperatures, e.g. above 300° C. or even 400° C., as is proposed in the prior art, is not only superfluous but also has an adverse effect on the activity of the catalyst. Sufficient drying routes are achieved by drying generally being carried out at elevated temperature, for example at at least 40° C., in particular at least 70° C. and especially ≧100° C.

Drying of the solid which has been impregnated with the ruthenium recursor is usually carried out under atmospheric pressure, but it is also possible to employ subatmospheric pressure to promote drying. A gas stream, e.g. air or nitrogen, is frequently passed over or through the material to be dried in order to promote drying.

The drying time naturally depends on the degree of drying desired and on the drying temperature and is generally in the range from 2 hours to 30 hours, preferably in the range from 4 hours to 15 hours.

The treated support material is preferably dried to such an extent that the content of water or of volatile solvent constituents is less than 5% by weight, in particular no more than 2% by weight and particularly preferably no more than 1% by weight, based on the total weight of the solid, prior to the reduction ii). Here, the proportions by weight indicated are based on the weight loss experienced by the solid at 300° C. and a pressure of 1 bar over a time of 10 minutes. The activity of the catalysts of the present invention can be increased further in this way.

The solid treated with the precursor solution is preferably kept in motion during drying, for example by drying the solid in a rotary tube oven or a rotary sphere oven. The activity of the catalysts of the present invention can be increased further in this way.

The conversion of the solid obtained after drying into its catalytically active form is, according to the present invention, carried out by hydrogenation of the solid in a manner known per se at the abovementioned temperatures (step (ii)).

For this purpose, the support material is brought into contact with hydrogen or a mixture of hydrogen and an inert gas at the abovementioned temperatures. The hydrogen partial pressure is of minor importance for the result of the reduction and will generally be varied in the range from 0.2 bar to 1.5 bar. The hydrogenation of the catalyst material is frequently carried out in a stream of hydrogen at atmospheric pressure. The solid obtained in i) is preferably kept in motion during the hydrogenation, for example by carrying out the hydrogenation of the solid in a rotary tube oven or a rotary sphere oven. The activity of the catalysts of the present invention can be increased further in this way.

Subsequent to the hydrogenation, the catalyst can be passivated in a known manner to improve handling, e.g. by briefly treating the catalyst with an oxygen-containing gas, e.g. air but preferably an inert gas mixture containing from 1 to 10% by volume of oxygen.

The catalysts of the present invention can be used as hydrogenation catalysts for many hydrogenation reactions which involve the hydrogenation of C=C, C=O and C=N double bonds or the hydrogenation of C≡C and C≡N triple bonds.

The catalysts of the present invention are particularly suitable for the hydrogenation of the carbonyl function of monosaccharides and oligosaccharides. In the hydrogenation of these substrates, they display, firstly, very high activities, so that high space-time yields, based on the catalyst used, in particular ruthenium used, are achieved. In addition, the corresponding sugar alcohols are obtained in high yields. Furthermore, the product selectivity is high, i.e. secondary reactions such as epimerization, decarbonylation, oligomerization and the like, which lead to losses in yield, occur to a lesser extent than in the case of the ruthenium catalysts of the prior art. The increased product selectivity also reduces the outlay required for isolating the desired hydrogenation product. Furthermore, the increased product selectivity makes a continuous reaction simpler. The catalysts of the present invention also display long operating lives, even under the aggressive conditions of a hydrogenation in an aqueous reaction medium, no drop or no appreciable drop in the activity of the catalysts of the present invention is observed even after prolonged use in the hydrogenation process of the present invention, e.g. after 1100 hours.

Of course, the catalysts used in this process can be regenerated by the known methods customary for noble metal catalysts such as ruthenium catalysts when their activity drops. This can be achieved, for example, by treatment of the catalyst with oxygen as described in BE 882279, treatment with dilute, halogen-free mineral acids as described in U.S. Pat. No. 4,072,628 or treatment with hydrogen peroxide, e.g. in the form of aqueous solutions having a concentration of from 0.1 to 35% by weight, or treatment with other oxidizing substances, preferably in the form of halogen-free solutions. After reactivation and before reuse, the catalyst will usually be rinsed with a solvent, e.g. water.

The invention therefore also provides a process for preparing sugar alcohols by catalytic hydrogenation of the corresponding monosaccharides and oligosaccharides, in particular the monosaccharides and disaccharides, in the liquid phase over a heterogeneous ruthenium catalyst, in which the heterogeneous ruthenium catalyst is selected from among ruthenium catalysts according to the present invention, with the exception of a process for preparing sorbitol which is subject matter of the parallel German patent application 10128203.6.

Suitable saccharides in principle include all known tetroses, pentoses, hexoses and heptoses, both aldoses and ketoses, and also their disaccharides and oligosaccharides, with the exception of glucose, fructose, gulose and sucrose, since they give sorbitol on hydrogenation. Monosaccharides which can be used in the process of the present invention include, for example: erythrose, threose, ribose, arabinose, xylose, lyxose, allose, altrose, mannose, gulose, idose, galactose, talose, erythrulose, ribulose, xylulose, psicose and tagatose, both the D form and the L form. Examples of disaccharides are: maltose, isomaltose, lactose, cellobiose and melobiose. The monosaccharides and oligosaccharides can be used as such or as mixtures, but the starting materials are preferably used in pure form.

Suitable monosaccharides and oligosaccharides for the hydrogenation process of the present invention are, in particular, the monosaccharides mannose for the preparation of mannitol, galactose for the preparation of dulcitol (galactitol) and xylose for the preparation of xylitol, preferably the D form of the monosaccharides, and the disaccharides maltose for the preparation of maltitol, isomaltulose (palatinose) for the preparation of isomaltitol and lactose for the preparation of lactitol. However, the other monosaccharides and oligosaccharides mentioned can also be hydrogenated in the presence of the ruthenium catalysts of the present invention to form the corresponding sugar alcohols. The hydrogenation of aldoses leads to sugar alcohols which have the same configuration in respect of the OH groups as the sugar used, and the hydrogenation of furanoses generally leads to mixtures of two diastereomeric sugar alcohols which differ only in the configuration of the carbon atom which bears the carbonyl function in the furanose. The respective pure sugar alcohol can generally be isolated from this mixture without problems.

The hydrogenation is preferably carried out by hydrogenation of a solution of the respective monosaccharide or oligosaccharide in an aqueous solvent. The term "aqueous" is employed here in the sense defined above.

Water is advantageously used as sole solvent, and may, if desired, contain small amounts of a preferably halogen-free acid for adjusting the pH. In particular, the monosaccharide or oligosaccharide is used as an aqueous solution having a pH in the range from 4 to 10, especially in the range from 5 to 7.

The concentration of starting materials in the liquid phase can in principle be chosen freely and is frequently in the range from 10 to 80% by weight and preferably in the range from 15 to 50% by weight, based on the total weight of the solution.

The actual hydrogenation using the catalysts of the present invention is usually carried out by a method analogous to known hydrogenation processes for the preparation of sugar alcohols, as are described in the prior art cited at the outset. For this purpose, the liquid phase comprising the starting material is brought into contact with the catalyst in the presence of hydrogen. The catalyst can either be suspended in the liquid phase to be hydrogenated (suspension process) or the liquid phase is passed over a fluidized catalyst bed (fluidized-bed process) or a fixed catalyst bed (fixed-bed process). The hydrogenation can be carried out either continuously or batchwise. The process of the present invention is preferably carried out in fixed-bed reactors operated in the downflow mode. The hydrogen can be passed over the catalyst either in concurrent with the solution of the starting material to be hydrogenated or in countercurrent.

Suitable apparatuses for carrying out a hydrogenation by the suspension method and for hydrogenations over a fluidized catalyst bed and over fixed catalyst bed are known from the prior art, e.g. from Ullmanns Enzyklopädie der Technischen Chemie, 4th Edition, Volume 13, p. 135 ff., and from P. N. Rylander, "Hydrogenation and Dehydrogenation" in Ullmann's Encyclopedia of Industrial Chemistry, 5th ed. on CD-ROM.

In general, the hydrogenation is carried out at a superatmospheric hydrogen pressure, e.g. at a hydrogen partial pressure of at least 10 bar, preferably at least 20 bar and in particular at least 40 bar. In general, the hydrogen partial pressure will not exceed a value of 500 bar, in particular 350 bar. The hydrogen partial pressure is particularly preferably in the range from 40 to 200 bar. The reaction temperatures are generally at least 40° C. and will frequently not exceed a value of 250° C. In particular, the hydrogenation process is carried out at from 80 to 150° C.

Owing to the high catalyst activity, relatively small amounts of catalyst based on the starting material used are required. Thus, less than 1 mol %, e.g. from $10^{-3}$ mol % to 0.5 mol %, of ruthenium are generally used per 1 mol of sugar in a batchwise suspension process. In the case of a continuous hydrogenation process, the starting material to be hydrogenated is usually passed over the catalyst in an amount of from 0.02 to 2 kg/(l(catalyst)*h) and preferably in an amount of from 0.07 to 0.7 kg/(l(catalyst)*h).

The following examples serve to illustrate the invention:

I. Production of the Catalysts of the Present Invention

1. Method A: Pulverulent, Halogen-free Catalyst, Not Calcined

A defined amount of the respective support material was impregnated with the maximum amount of a solution of ruthenium(III) nitrosyl nitrate in water which could be taken up by the respective support material. The maximum amount able to be taken up by the respective support material was determined beforehand on an authentic sample. The concentration of the solution was in each case calculated so that the desired concentration of ruthenium in the support material resulted.

The solid obtained in this way was subsequently dried at 120° C. for 13 hours in a drying oven. The residual water content was below 1% by weight (determined as the weight loss of a sample dried at 300° C. under 1 bar for 10 minutes).

The solid obtained in this way was reduced at 300° C. in a stream of hydrogen under atmospheric pressure for 4 hours in a reaction tube. After cooling and blanketing with nitrogen, the catalyst was passivated by passing 5% by volume of oxygen in nitrogen over it for a period of 2 hours.

2. Method B: Pulverulent, Halogen-free Catalyst, Kept in Motion During Drying, Not Calcined The procedure of method A was repeated, but drying was carried out in a rotary sphere oven. The residual water content was below 1% by weight.

3. Method C: Pulverulent, Halogen-free Catalyst, Calcined

The procedure of method B was repeated, but the solid obtained after drying was heated at 400° C. in a stream of air for 4 hours prior to the hydrogenation.

4. Method D: Pulverulent, Halogen-containing Catalyst, Not Calcined

The procedure of method B was repeated using ruthenium (III) chloride in place of ruthenium(III) nitrosyl nitrate.

5. Method E: Halogen-free Catalyst in the Form of Extrudates, Not Calcined

A defined amount of cylindrical support material extrudates (diameter: 4 mm, length: 3-10 mm) was impregnated with the maximum amount of a solution of ruthenium(III) nitrosyl nitrate in water which could be taken up by the respective support material. The maximum amount able to be taken up by the respective support material was determined beforehand on an authentic sample. The concentration of the solution was in each case calculated so that the desired concentration of ruthenium in the support material resulted.

The impregnated extrudates obtained in this way were subsequently dried at 120° C. for 13 hours in a rotary sphere oven. The residual water content was below 1% by weight.

The dried extrudates obtained in this way were reduced at 300° C. in a stream of hydrogen under atmospheric pressure for 4 hours in a rotary sphere oven. After cooling and blanketing with nitrogen, the catalyst obtained in this way was passivated by passing 5% by volume of oxygen in nitrogen over it for a period of 2 hours.

TABLE 1

Catalysts

| Catalyst No. | Ruthenium content [% by weight] | Method | Support |
|---|---|---|---|
| C1 | 5 | B | $SiO_2$ powder[1] |
| C2 (comp.) | 5 | D | $SiO_2$ powder[1] |
| C3 | 5 | A | $SiO_2$ powder[1] |
| C4 (comp.) | 5 | C | $SiO_2$ powder[1] |
| C5 (comp.) | 5 | B | $\alpha$-$Al_2O_3$ powder[2] |
| C6 (comp.) | 5 | B | $\theta$-$Al_2O_3$ powder[3] |
| C7 (comp.) | 5 | B | $TiO_2$ powder[4] |
| C8 | 1 | E | $SiO_2$ extrudates[5] | comp. comparative catalyst

[1] Silica gel powder having an $SiO_2$ content of > 99.95% by weight, a specific BET surface area of 523 $m^2$/g, a water uptake of 1.4 ml/g, a pore volume of 0.75 ml/g (determined by nitrogen porosimetry in accordance with DIN 66134), a defined pore size of 60 Å, a particle size of from 63 to 200 μm;
[2] alpha-Aluminum oxide powder having an $Al_2O_3$ content of > 99.95% by weight, a specific BET surface area of 7 $m^2$/g, a water uptake of 0.84 ml/g, a particle size of < 100 μm;
[3] theta-Aluminum oxide powder having an $Al_2O_3$ content of > 99.95% by weight, a specific BET surface area of 80 $m^2$/g, a water uptake of 1.05 ml/g, a pore volume of 0.67 ml/g (DIN 66134), a particle size of < 100 μm;
[4] Titanium dioxide powder having a $TiO_2$ content of > 99.9% by weight, a specific BET surface area of 325 $m^2$/g, a water uptake of 0.84 ml/g, a particle size of < 63 μm;
[5] Silica gel extrudates (d = 4 mm, l = 1-10 mm) comprising silica gel having an $SiO_2$ content of > 99.5% by weight (0.3% by weight of $Na_2O$), a specific BET surface area of 169 $m^2$/g, a water uptake of 0.95 ml/g, a pore volume of 0.7 ml/g (DIN 66134).

II. Hydrogenation of Xylose Using a Suspended Catalyst

EXAMPLES 1 AND 2, COMPARATIVE EXAMPLES COMP. 1 to COMP. 5

General hydrogenation method 1200 ml of a 30% strength by weight solution of xylose in water together with 3 g of the respective catalyst were placed in a 2.5 l autoclave fitted with stirrer, sampling facilities and a pressure regulator for hydrogen. The autoclave was filled with nitrogen. It was subsequently pressurized with 100 bar of hydrogen and heated to 90° C. During the reaction, the reaction mixture was stirred at 1000 rpm. To determine the conversion during the reaction, samples were taken at regular intervals and analyzed by means of HPLC to determine the contents of xylose, xylitol and other products. The reaction was stopped after not more than 10 hours. Table 2 indicates the time required to reach a maximum yield. The table also shows the selectivity in respect of the formation of xylitol, which could be determined to an accuracy of about 0.5% (absolute).

TABLE 2

| Example | Cat. No. | Support | t max. [h] | Conversion [%] | Selectivity [%] |
|---|---|---|---|---|---|
| 1 | C1 | SiO$_2$ powder | 3 | 99.85 | >98.5 |
| Comp. 1 | C2 (comp.) | SiO$_2$ powder | 7 | 99.85 | >98.5 |
| 2 | C3 | SiO$_2$ powder | 5 | 99.95 | >98.5 |
| Comp. 2 | C4 (comp.) | SiO$_2$ powder | 10 | 99.96 | >98.5 |
| Comp. 3 | C5 (comp.) | α-Al$_2$O$_3$ powder | 10 | 94.15 | 98.5 |
| Comp. 4 | C6 (comp.) | θ-Al$_2$O$_3$ powder | 10 | 99.53 | >98.5 |
| Comp. 5 | C7 (comp.) | TiO$_2$ powder | 10 | 76.84 | 98.2 |

The results show that the catalysts of the present invention have better reactivities combined with comparable or better selectivities than catalysts not according to the present invention.

III Hydrogenation of Mannose, Maltose and Lactose Using a Suspended Catalyst

EXAMPLES 3, 4 AND 5

Using a procedure analogous to the general hydrogenation method indicated under II, 1200 ml of a 30% strength solution of the respective monosaccharide or disaccharide in water were hydrogenated at 120° C. under 50 bar of hydrogen in the presence of 3 g of the respective catalyst. Conversion and selectivity were determined by means of HPLC as described under II. Table 3 indicates the time required to reach a maximum conversion (>99.8%). Also shown is the selectivity in respect of the formation of the desired sugar alcohol.

TABLE 3

| Example | Cat. No. | Starting material | Product | t max. [h] | Conversion [%] | Selectivity [%] |
|---|---|---|---|---|---|---|
| 3 | C1 | Mannose | Mannitol | 2 | >99.8 | 96 |
| 4 | C1 | Maltose | Maltitol | 1 | >99.8 | 69 |
| 5 | C1 | Lactose | Lactitol | 3 | >99.8 | 87 |

III Hydrogenation of Xylose and Lactose Over a Vixed Catalyst Bed

EXAMPLES 6 AND 7

The reactor employed was a heatable stainless steel reaction tube which was charged with catalyst C8. The reaction apparatus also included a feed pump for the starting materials, a circulation pump, sampling facilities and a separator with a level regulator and an offgas regulator.

In this reaction apparatus, a 30% strength by weight solution of the respective monosaccharide or disaccharide was circulated at 100° C. and a hydrogen pressure of 50 bar at a rate of 50 ml/(g(catalyst)*h), and during this procedure the decrease in the concentration of the starting material, the increase in the concentration of the products and the formation of by-products was determined by analysis as described under II. When a conversion of 99.4% had been reached, the reaction was stopped. The contact time required to reach the maximum conversion is indicated in table 4 together with the selectivity.

Contact time=vol.(solution)/vol.(reaction tube)*reaction time

TABLE 4

| Example | Starting material | Product | Contact time [h] | Selectivity [%] |
|---|---|---|---|---|
| 6 | Xylose | Xylitol | 0.81 | 97.2 |
| 7 | Lactose | Lactitol | 1.0 | 94.1 |

We claim:

1. A ruthenium catalyst, obtainable by:
   i) treating a support material based on amorphous silicon dioxide comprising at least 95% by weight of silicon dioxide and less than 1% by weight aluminum oxide, calculated as Al$_2$O$_3$, one or more times with a halogen-free aqueous solution of a low molecular weight ruthenium compound, which does not contain halogen, and which is a ruthenium (III) salt or a metal ruthenate and subsequently drying the treated support material at a temperature below 200° C., and
   ii) reducing the solid obtained in i) by means of hydrogen at a temperature ranging from 100 to 350° C.,
   wherein step ii) is carried out directly after step i), and wherein the ruthenium content in the catalyst ranges from 0.1 to 5% by weight, based on the support material.

2. The ruthenium catalyst as claimed in claim 1, wherein the support based on amorphous silicon dioxide has a BET surface area in the range of 50 to 700 m$^2$/g.

3. The ruthenium catalyst as claimed in claim 1, wherein the ruthenium compound is selected from the group consisting of ruthenium(III) nitrosyl nitrate, ruthenium(III) acetate, sodium ruthenate(IV) and potassium ruthenate(IV).

4. The ruthenium catalyst as claimed in claim 1, wherein the solid which is obtained from step i) and reduced in step ii) has a water content of less than 5% by weight, based on the total weight of the solid.

5. The ruthenium catalyst as claimed in claim 1, wherein drying in step i) is carried out with the treated support material being kept in motion.

6. The ruthenium catalyst as claimed in claim 1, containing less than 0.05% by weight of halogen, based on the total weight of the catalyst, and
   wherein the ruthenium is present in atomically disperse form and/or in the form of ruthenium particles on the support, where the form of ruthenium particles and/or agglomerates have diameters above 10 nm.

7. A process for producing a ruthenium catalyst as claimed in claim 1, which comprises the following steps:
i) treating a support material based on amorphous silicon dioxide having a BET surface area in the range of 50 to 700 m$^2$/g and comprising at least 90% by weight of silicon dioxide and less than 1% by weight aluminum oxide, calculated as $Al_2O_3$, one or more times with a halogen-free aqueous solution of a low molecular weight ruthenium compound and subsequently drying the treated support material at a temperature below 200° C., and
ii) reducing the solid obtained in i) by means of hydrogen at a temperature ranging from 100 to 350° C.,
wherein step ii) is carried out directly after step i), and wherein the ruthenium content in the catalyst ranges from 0.1 to 5% by weight, based on the support material.

8. A process for preparing sugar alcohols, comprising: catalytically hydrogenating the corresponding monosaccharides and oligosaccharides in the liquid phase over a heterogeneous ruthenium catalyst, with the exception of the preparation of sorbitol, wherein the heterogeneous ruthenium catalyst is selected from the group consisting of the ruthenium catalyst as claimed in claim 1.

9. The process as claimed in claim 8, wherein the monosaccharide or oligosaccharide is in the form of an aqueous solution having a pH in the range of 4 to 10.

10. The process as claimed in claim 8, wherein the hydrogenation is carried out at a hydrogen partial pressure in the range of 10 to 500 bar.

11. The process as claimed in claim 8, wherein the hydrogenation is carried out at a temperature ranging from 40 to 250° C.

12. The process as claimed in claim 8, wherein the hydrogenation is carried out over a fixed catalyst bed.

13. The process as claimed in claim 8, wherein the hydrogenation is carried out in a liquid phase in which the catalyst is present in the form of a suspension.

* * * * *